United States Patent [19]
Crause et al.

[11] Patent Number: 5,866,399
[45] Date of Patent: Feb. 2, 1999

[54] PROCESS FOR INACTIVATING CARBOXYPEPTIDASE Y IN HIRUDIN-CONTAINING CULTURE BROTHS

[75] Inventors: Peter Crause, Offenbach; Paul Habermann, Eppstein; Jörg Möller, Soden; Wolfgang Ulmer, Eppstein, all of Germany

[73] Assignee: Hoechst Aktiengesellschaft, Frankfurt, Germany

[21] Appl. No.: 695,434

[22] Filed: Aug. 12, 1996

[30] Foreign Application Priority Data

Aug. 16, 1995 [DE] Germany ................ 195 29 997.3

[51] Int. Cl.⁶ ................ C12N 9/50; C12N 1/14; A23J 1/00; C12M 1/32
[52] U.S. Cl. ............... 435/219; 435/254.21; 435/293.1; 530/427
[58] Field of Search ............ 435/254.21, 255.1, 435/255.2, 803, 813, 814, 71.1, 212, 219, 195, 69.1, 69.2, 293.1; 530/412, 427

[56] References Cited

U.S. PATENT DOCUMENTS

| | | | |
|---|---|---|---|
| 4,256,590 | 3/1981 | Naslund et al. | 507/213 |
| 4,299,848 | 11/1981 | De Stefanis et al. | 426/20 |
| 4,455,290 | 6/1984 | Olexa et al. | 424/1.69 |
| 4,632,780 | 12/1986 | Seidah et al. | 530/306 |
| 5,422,249 | 6/1995 | Liersch et al. | 435/69.2 |
| 5,455,054 | 10/1995 | Bryson et al. | 426/106 |

FOREIGN PATENT DOCUMENTS

| | | |
|---|---|---|
| 0 158 564 B1 | 10/1985 | European Pat. Off. |
| 0 158 986 B1 | 10/1985 | European Pat. Off. |
| 0 168 342 | 1/1986 | European Pat. Off. |
| 0 168 342 B1 | 1/1986 | European Pat. Off. |
| 0 171 024 B1 | 2/1986 | European Pat. Off. |
| 0 193 175 | 9/1986 | European Pat. Off. |
| 0 200 655 B1 | 11/1986 | European Pat. Off. |
| 0 324 712 B1 | 7/1989 | European Pat. Off. |
| 0 341 215 B1 | 11/1989 | European Pat. Off. |
| 0 390 676 B1 | 10/1990 | European Pat. Off. |
| 3342199A1 | 5/1984 | Germany |
| 34 45 517 C2 | 6/1986 | Germany |
| 2 249 096 | 4/1992 | United Kingdom |

OTHER PUBLICATIONS

Halasz et al., "Proteolytic Enzyme Activity of S. Cerevisiae Baker's Yeast And S. Carlsbergensis Brewer's Yeast", *Acta Alimentaria*, vol. 22(3):193–209, (1993).

Kuhn et al., "Isolation And Partial Characterization Of An Acid Carboxypeptidase From Yeast", *Biochemistry*, vol. 13(19):3871–3877, (1974).

Chang, "Stability of Hirudin, A Thrombin–Specific Inhibitor", *The Journal of Biological Chemistry*, vol. 266(17):10839–10843, (1991).

Markwardt, "Pharamacology of Hirudin:One Hundred Years After the First Report of the Anticoagulant Agent in Medicinal Leeches", Biomed. Biochim. Acta 44, (1985) pp. 1007–1013.

Marki et al., "Recombinant Hirudin:Genetic Engineering and Structure Analysis", Seminars in Thrombosis and Hemostasis, vol. 17, No. 2, (1991) pp. 88–93.

Tijssen, "Practice and Theory of Enzyme Immunoassays:Laboratory Techniques in Biochemistry and Molecular Biology", vol. 15, (1985) pp. 9–384.

Dodt, "The Complete Covalent Structure of Hirudin", Biol. Chem. Hoppe–Seyler, vol. 366, (1985) pp. 379–385.

*Primary Examiner*—Jean C. Witz
*Assistant Examiner*—Susan Hanley
*Attorney, Agent, or Firm*—Foley & Lardner

[57] ABSTRACT

The present invention relates to a process for inactivating Carboxypeptidase Y (CPY) in a hirudin-containing culture broth produced by fermenting a transformed yeast. It has been found that inactive precursors of CPY are activated at a temperature 70° C. and that the active peptidases will further degrade hirudin when the two proteins are present together in a composition. The present invention overcomes the CPY activation problem by heating a broth containing hirudin and CPY to a temperature of about 80°–100° C. in about one minute or less.

20 Claims, No Drawings

PROCESS FOR INACTIVATING CARBOXYPEPTIDASE Y IN HIRUDIN-CONTAINING CULTURE BROTHS

FIELD OF THE INVENTION

The present invention relates to a process for inactivating carboxypeptidase Y (CPY) in a hirudin-containing culture broth produced by fermenting a transformed yeast.

BACKGROUND OF THE INVENTION

The polypeptide hirudin, originally isolated from the leech Hirudo medicinalis, is a highly specific thrombin inhibitor of broad therapeutic potential. F. Markwardt, Biomed. Biochim. Acta 44: 1007–1013 (1985). However, the amounts required can only be produced by genetic engineering methods by means of transformed microorganisms. It has been found that the yeast Saccharomyces cerevisiae is suitable as a host organism for producing correctly folded and fully active hirudin. EP A1 168 342; EP A1 200 655.

The yeast Saccharomyces cerevisiae, which is particularly preferably used for producing recombinant peptides and proteins by genetic engineering, forms the enzyme carboxypeptidase Y (CPY). CPY is a thermally unstable molecule. See Kuhn et al., "Isolation and Partial Characterisation of an Acid Carboxypeptidase from Yeast," Biochemistry, 13(19): 3871–77 (1974). A 5-minute heat treatment at 68° C. and pH=7.0 leads to complete inactivation of CPY, and lower temperatures lead to partial inactivation of CPY.

This enzyme non-specifically cleaves off various amino acids from the C terminus of proteins and can therefore be used for determining the carboxy-terminal sequence of proteins. Obviously, this enzyme is also able to break down proteins of value expressed in the yeast, including pharmacologically active compounds such as hirudin, during the production process, in particular during chromatographic purification. This leads to the formation of by-products and losses of yield, which can be significant. In addition, CPY can reduce the stability of high-purity products if it is still present in traces in a preparation, e.g., if it is present in a lyophilizate.

Hirudin has a free C terminus and is therefore exposed substantially unprotected to enzymatic attack by CPY.

One solution to this problem is to use mutant yeast strains in which the CPY activity is suppressed or eliminated by various methods. See, for example, EP 390 676, EP 341 215 and GB 2 249 096. However, these methods necessitate a relatively great change in the yeast strain which may possibly restrict the growth behavior and/or alter the physiological stability of the microorganisms.

CPY can also be inhibited by chemical inhibitors, e.g., by phenylmethylsulfonyl fluoride (PMSF). A chemical inhibition of this type is undesirable, at least in the case of pharmaceutically active compounds, since it can lead to partial derivatization which is sometimes undetectable.

Thus, there is a need for a process for inactivating CPY in hirudin-containing culture broths that does not have the drawbacks of the above-mentioned methods. There also is a need for a means for performing this process on a large scale, for example, on an industrial scale.

SUMMARY OF THE INVENTION

It is an object of the present invention, therefore, to provide a process for inactivating carboxypeptidase Y (CPY) in hirudin-containing culture broths that is suitable for use on an industrial scale.

In accomplishing this and other objects, the present invention provides a process for inactivating carboxypeptidase Y in a hirudin-containing culture broth, which comprises the step of rapidly heating a culture broth comprising CPY and hirudin to a temperature of from about 80° C. to about 100° C.

In one embodiment of the invention, the culture broth is rapidly heated through a temperature at which activation of CPY from inactive precursors occurs to a temperature of from about 80° C. to about 100° C., at which inactivation of CPY occurs, thereby minimizing the activation of CPY from inactive precursors.

In another embodiment of the invention, the culture broth is heated to a temperature of from about 80° C. to about 100° C. within about 60 seconds.

In another embodiment of the invention, the culture broth is heated to a temperature of from about 80° C. to about 100° C. in about 40 to about 60 seconds.

In another embodiment of the invention, the process further comprises the step of cooling the heated broth to room temperature.

In another embodiment of the invention, the process comprises flowing the culture broth through a tubular apparatus comprising a heating section, a holding section and a cooling section.

Additional objects and advantages of the invention will be set forth in part in the description that follows, and in part will be obvious from the description, or may be learned by practice of the invention. The objects and advantages may be realized and obtained by means of the processes and apparatus particularly pointed out in the appended claims.

DETAILED DESCRIPTION

The present invention provides a process for inactivating carboxypeptidase Y (CPY) in a hirudin-containing culture broth produced by fermenting a transformed yeast, with high retention of hirudin, utilizing the contrasting thermal stability properties of CPY, which is thermally instable, and hirudin, which is thermally stable.

The 7,000 dalton protein hirudin, which is expressed by the yeast Saccharomyces cerevisia and is secreted into the culture medium, in contrast to CPY, has a remarkable thermal stability. Jui-Yoa Chang, "Stability of Hirudin, a Thrombin-specific Inhibitor," J. Biol. Chem., 266(17): 10839–43 (1991). For example, after treatment for 30 minutes at 95° C. and pH=8.0, 95% of the initial hirudin activity is still recovered.

The present inventors' small-scale laboratory experiments on hirudin-containing fermentation broths from transformed yeasts in a glass flask have shown that a temperature of 60° C. activates CPY, apparently from inactive precursors of the enzyme. This leads to an intensified enzymatic CPY attack on the exposed C-terminus of hirudin and to the formation of hirudins shortened at the C terminus. On the other hand, heating to 80° C. leads to increased by-product formation as a result of chemical breakdown of the hirudin. Heating to 70° C. in the course of 10 minutes with a subsequent inactivation time of 20 minutes and subsequent cooling to room temperature leads to inactivation of the CPY with high hirudin recovery.

From these experiments, the present inventors developed a means for achieving reliable inactivation of CPY with high retention of active hirudin product that can be implemented on an industrial scale. While the above-described temperature and time parameters are suitable for small-scale (i.e., laboratory bench-scale) inactivation of CPY in hirudin-containing broth, they were not found to be effective when larger amounts of broth are to be inactivated. The present inventors found that, with a large-scale process, a heat treatment temperature of 70° C. leads to a sharp increase in activity of CPY, combined with an increased breakdown of hirudin. At 75° C., a residual activity of CPY of approximately 2% of the original value is still observed, and at 80° C., a residual CPY activity of approximately 0.5% is observed. Temperatures between about 85° C. and about 95° C., such as temperatures from 85° C. to 95° C., decrease the initial activity of CPY to approximately 0.1% and give a product yield of hirudin of 95%, with even quantitative yields of hirudin being sometimes obtained. The hirudin product solutions treated in this manner are stable and do not display further enzymatic breakdown. Only at temperatures>100° C. does chemical breakdown lead to high product losses of hirudin.

Thus, the present inventors found that heating the broth to a temperature of from about 80° C. to about 100° C. is effective in inactivating the CPY while maintaining the activity of the hirudin. Moreover, the present inventors found that rapidly heating the culture broth to the desired temperature range avoids the above-described problem of activating the CPY from inactive precursors. For example, the present inventors have found that bringing the broth to the desired temperature in about 60 seconds or less avoids this problem.

A process requiring culture broth to be heated to a narrow temperature range in a short period of time does not lend itself easily to an industrial process. For example, when heating large volumes of broth in, for example, a vat, the heat is unevenly distributed, even in a stirred tank, because of the volume dependency of the heating and cooling processes. Thus, in some portions of the broth the heating may be insufficient to inactivate the CPY, and may even result in the activation of CPY due to the above-described temperature-dependant activation of CPY from inactive precursors. In other portions of the broth, the heating may be excessive, leading to breakdown of hirudin. Moreover, it is difficult to ensure that a large volume of broth is brought to the desired temperature range within a short period of time, such as within about 60 seconds.

The present inventors have found that by following the guidelines set forth herein, acceptable processes can be accomplished, for example, by a continuous treatment of the broth in flow-through heat exchangers, which provide a considerably broader safe process area. Nevertheless, those skilled in the art can envision batch processes which can be used in place of the continuous process described herein, and such batch processes are encompassed by the present invention.

The present invention is described in detail below, with reference to specific, acceptable embodiments. The skilled artisan will readily appreciate other acceptable embodiments.

As used herein, the term hirudin means peptide thrombin inhibitors which are derived from the known isohirudins of the species Hirudo medicinalis and have the essential structural features of these, in particular the characteristic linkage of the three disulfide bridges. J. Dodt et al., Biol. Chem. Hoppe-Seyler 366: 379–85 (1985). Cf., e.g., EP A1 158 564, EP A1 168 342, DE 34 45 517, EP A2 193 175, EP A1 200 655, EP A1 158 986, EP A1 209 061, DE 33 42 199, and EP A1 171 024. In particular, a hirudin as described in EP A 1 171 024, EP A1 158 986 and EP A1 209 061 is an acceptable hirudin in accordance with the present invention. Such hirudins can have a range of specific activities. Advantageously, the specific activity of the substantially purified hirudin can be at least about 10,000 AT-U/mg, and advantageously at least 10,000 AT-U/mg.

In one embodiment, the process of the invention is useful for inactivating CPY in a culture broth which contains a hirudin derivative having the amino acid sequence disclosed in EP 0 324 712 ([Leu$^1$, Thr$^2$]-63-desulfohirudin).

As used herein, the term hirudin-containing culture broth means any culture broth obtained from transformed yeast, that is, any culture broth obtained from yeast transformed so as to produce hirudin. Hirudin-containing culture broths from Saccharomyces cerevisiae are acceptable for use in accordance with the present invention.

The pH of the culture broth used in accordance with the process of the present invention may be from about 6.2 to about 6.5. For example, the pH may be from 6.2 to 6.5.

As used herein, the phrase tubular apparatus means any tubular apparatus that the broth can be flowed through. The tubular apparatus advantageously comprises a heating section. As the broth flows through the heating section it is rapidly heated to the desired temperature range. The tubular apparatus may further comprise a holding section, where the broth may be maintained at the elevated temperature, and may further comprise a cooling section, where the broth may be cooled to room temperature. Tubular apparatus suitable for use in the present invention are known, and those skilled in the art can select specific apparatus for use based on the teachings set forth herein. Advantageously, the tubular apparatus is a heat exchanger.

The process of the present invention comprises the step of rapidly heating the culture broth to a temperature of from about 80° C. to about 100° C., with the range of from about 85° C. to about 95° C. being acceptable, and with the temperature of about 85° C. also being acceptable. For example, the broth may be heated to a temperature of from 80° C. to 100° C., acceptably from 85° C. to 95° C., or acceptably to 85° C.

The culture broth is brought to the desired temperature range rapidly. As discussed above, rapid heating avoids the heat-dependent activation of CPY from its inactive precursors. Thus, the culture broth is brought rapidly through a temperature at which this activation of CPY occurs to a temperature at which inactivation of CPY occurs. For example, the culture broth is heated rapidly through a temperature of about 70° C., to a temperature of from about 80° C. to about 100° C., with the broth reaching the desired temperature range in, for example, about 60 seconds or less. Advantageously, the desired temperature range is reached in from about 40 to about 60 seconds, for example, in from 40 to 60 seconds.

The culture broth may be heated by any means. For example, the culture broth can be heated by means of microwaves. The broth is heated for a period of time sufficient to achieve at least partial inactivation of CPY present in the broth.

As discussed above, apparatus comprising flow-through heat exchangers are acceptable for use in accordance with the present invention. For example, an apparatus for carrying out the process of the present invention for inactivating CPY may comprise a tubular apparatus comprising a heating section. The tubular apparatus may further comprise a holding and/or inactivation section, and a cooling section.

In one embodiment, the apparatus comprises (1) a heatable tube, which may optionally be equipped with static mixers, as a heating-up section, for example a flow-through heat exchanger, in which the culture broth is rapidly brought to the preferred temperature range; (2) an insulated tube as a holding or inactivation section, in which the culture broth is held at the preferred temperature range and (3) a cooled tube, for example a flow-through heat exchanger, as a cooling section, in which the culture broth is cooled to room temperature.

In one embodiment, therefore, the present invention provides a process for inactivating carboxypeptidase Y in a hirudin-containing culture broth produced by fermenting a transformed yeast, which comprises continuously heating the culture broth by flowing it through a tubular apparatus which has a heating section, a holding section and a cooling section, to a temperature of from about 80° C. to about 100° C., with a temperature of from about 85° C. to about 95° C. being acceptable, and with a temperature of about 85° C. also being acceptable. For example, the culture broth may be heated to a temperature of from 80° C. to 100° C., preferably from 85° C. to 95° C., particularly preferably to a temperature of 85° C.

The rapid heating of the culture broth may be reflected in the mean time the culture broth resides in the heating section of the tubular apparatus. For example, the culture broth may have a mean residence time in the heating section of about 60 seconds or less, for example, of from about 40 to about 60 seconds, advantageously of from 40 to 60 seconds. The mean residence time can be set by the apparatus design and the flow rate of the culture broth.

As discussed above, the culture broth may be heated to the preferred temperature range by any means. For example, the culture broth can be heated in the heating section of the apparatus by means of microwaves. Also as described above, the culture broth is maintained at the elevated temperature for a period of time sufficient to achieve at least partial inactivation of CPY present in the broth.

By flowing the culture broth through a tubular apparatus as described above, it is possible to heat the broth to the desired temperature range within the desired amount of time in order to achieve inactivation of the CPY while maintaining the activity of the hirudin.

Advantageously, the apparatus is initially started up with demineralized, filtered water. As soon as the preferred temperature range is reached at the end of the heating section, the inflow is changed from water to the culture broth. After inactivation of the culture broth by heating in the apparatus as described above, the apparatus is advantageously run empty under operating conditions with demineralized, filtered water, in order to minimize product losses in the system. Advantageously, only after this step is the heating shut off.

Since the culture broth used in the process of the present invention may only have been preliminarily purified, in addition to the hirudin product, various other proteins/by-products and nucleic acids and other organic and inorganic constituents may still be present in the solution to be inactivated. In order to prevent deposits and burn-on on the heat exchanger surfaces, which can impede heat transport and reduce the temperature, the heating-up section of the apparatus used in accordance with the present invention advantageously comprises those heat exchangers in which the inner surface is continuously mechanically cleaned.

For example, so-called scraped-surface heat exchangers are acceptable for use. These are commercially available and are used industrially, for example, for pasteurizing fruit juices or dairy products. In these apparatuses, scrapers made of synthetic resin run on a shaft within the heater tube and are pressed onto the tube walls by the centrifugal force, as a result of which burn-on is continuously removed. Other devices for preventing deposits and burn-on on the inner heat exchanger surfaces also can be used in the process according to the present invention.

Alternatively, skilled artisans readily will envision batch processes which may be used in place of the continuous process described above.

By employing the inactivation method of the present invention, the work-up and purification of hirudin-containing solutions is made possible for the first time, without changing the production strain by mutation and/or genetic engineering methods and without contaminating the solutions by the action of chemical inhibitors.

The embodiments of the invention may be further illustrated through examples which show aspects of the invention in detail. These examples illustrate specific elements of the invention and are not to be construed as limiting the scope thereof.

EXAMPLES

The examples below use culture broths produced by fermenting transformed yeasts which contain the hirudin derivative having the amino acid sequence disclosed in EP 0 324 712 ([Leu$^1$, Thr$^2$]-63-desulfohirudin). However, the same advantageous results are also obtained with other hirudins, such as the other hirudins mentioned above.

General instructions:

The solution to be inactivated, which, as a result of precipitation is cloudy, and has been cooled to temperatures T≦10° C., was adjusted to a pH of pH=6.4 ±0.1 with acetic acid or sodium hydroxide solution.

The apparatus for heat inactivation, comprising a scraped-surface heat exchanger from APV Crepaco, Type 1HO-648S/CP 508 as heater, a holding section and a cooler, was then run up to operating temperature with demineralized, filtered water (purified water). The mean residence times in the individual sections of the heat exchanger were set by means of the chosen flow rate and determined using traces experiments (pulsed addition of a fluorescent dye and detection using a fluorescence sensor). As soon as the desired temperature (±1° C.) had been achieved at the end of the heater, the inflow was changed from water to product solution. After inactivation of the solution, the apparatus was in turn run empty under operating conditions with demineralized, filtered water (purified water), in order to minimize product losses in the system; only after this step was the heating turned off. The suspension was filtered to separate off precipitate which was deposited in the heat treatment.

The CPY concentrations were determined by means of the ELISA described below:

The CPY ELISA was carried out in principle by processes known to those skilled in the art. P. Tijssen, "Practice and Theory of Enzyme Immunoassays," in Laboratory Techniques in Biochemistry and Molecular Biology, Burdon, et al., eds., Vol. 15 (Elsevier, 1985).

The following reagents were used:

Coating buffer: NaH$_2$PO$_4$·2H$_2$O 0.315 g Na$_2$HPO$_4$·2H$_2$O 1.2 g Sodium azide 0.5 g
made up to 1 liter with water.

Blocking buffer; 1 g of bovine serum albumin (BSA)/1l of PBS (phosphate buffered saline)

MSTB buffer: MOPS (morpholino-propanesulfonic acid) 10.45 g SDS 1.0 g Triton X-100 1.0 g BSA 12.5 g made up to 500 ml with water, adjusted to pH 7.4 with NaOH.

Washing buffer: 0.5 g of Tween 20/1 of PBS

Conjugate buffer: Mikrobiol for Enzygnost®, Behringwerke Marburg, Order No. OUWW TMB (tetramethylbenzidine) Combipack (additional reagents for Enzygnost®/TMB), Behringwerke Marburg, Order No. OUVP 10/11

CPY: Carboxypeptidase (yeast), 135 U/mg, e.g. Serva Heidelberg, Order No. 16137

Coating antibody: Sheep anti-CPY, prepared by processes known to those skilled in the art Detection antibody: Rabbit anti-CPY, prepared by processes known to those skilled in the art, labeled with peroxidase.

Procedure:

Microtest plates were filled with coating antibody (5 μg/ml in coating buffer, 100 μl/well) and incubated at 10° C. for at least 7 days. The coating solution was then removed and 200 μl of blocking buffer/well were added and the plates were incubated at 37° C. for 90 min. The CPY samples were then applied. In each experiment, a standard series was included (1 μg/ml–0.002 ng/ml of CPY in MSTB buffer, 1:3 dilutions).

The unknown samples were prediluted in MSTB buffer as a function of the expected CPY concentration. After the blocking buffer was removed, all samples were applied to the plates at 100 μl/well. The plates were then incubated at 37° C. for 90 min. The plates were then washed three times with washing buffer. The detection antibody was diluted in a suitable manner, e.g. 1:10,000, in Mikrobiol buffer+1% standard rabbit serum and 100 μl thereof was pipetted into each well. The plates were then incubated at 37° C. for 90 min and then washed three times with washing buffer.

The bound peroxidase was detected using the reagents from the Combipack (additional reagents for Enzygnost®/TMB). The TMB chromogen was diluted 1:20 in buffer/substrate and heated to room temperature. 100 μl of this was added to each well of the plates. The plates were then incubated for 30 min at room temperature and protected against the action of light. The reaction was then stopped by adding 100 μl of 0.5M $H_2SO_4$ and color development was measured in a plate photometer at 450 nm. The CPY concentration in the unknown samples was calculated on the basis of the standard series using a suitable computer program such as KinetiCalc® from Tecnomara, Fernwald.

Example 1

The inactivation of CPY by heat treatment in accordance with the present invention was evaluated. The steps of heating up to inactivation temperature, inactivation and cooling to room temperature were conducted with the solution to be inactivated having a mean residence time in the respective sections of the apparatus of up to 60 seconds. The mean residence times were set by the apparatus design (throughput 400 l/h±20 l/h). The results listed below were obtained using the following mean residence times:

Heating-up section: 50 sec

Inactivation section: 28 sec

Cooling section: 12 sec

TABLE 1

Inactivation of CPY at Various Temperatures

| Temperature | CPY [ng/ml] |
|---|---|
| 75° C. | 16.3 |
| 80° C. | 4.1 |
| 85° C. | 1.1 |
| 90° C. | 0.9 |
| 95° C. | 1.0 |
| Original sample | 760 |

The CPY concentrations of the samples were determined by ELISA. The detection limit of this test was 0.5 ng/ml.

Example 2

The effect of mean residence time on the inactivation of CPY in accordance with the process of the present invention was studied. By varying the throughput, various residence times were set in the heating-up section in the apparatus described in the general instructions. The temperature at the end of the heating-up section and in the inactivation section was 85° C. Table 2 shows CPY concentrations determined by ELISA after treatment of the culture broth with different mean residence times in the heating-up section.

TABLE 2

CPY Concentration After Inactivation At 85° C.
(varied mean residence times or heating-up times)

| Throughput [l/h] | mean residence time [s] | CPY [ng/ml] |
|---|---|---|
| 340 | 59 | 1.13 |
| 400 | 50 | 1.2 |
| 500 | 40 | 1.16 |

Example 3

The effect of the inactivation process of the present invention on the hirudin in the inactivated solution was studied. Hirudin-containing culture broths were treated at various temperatures by the process described in the general instructions, and the hirudin content after sterile filtration (0.2 μm filter) was determined in each case immediately and after storage of the samples for 8 days at 2° to 8° C. by HPLC (conditions: stationary phase: LiChrospher® 300 RP-18, 10 μm (Merck); mobile phase A: acetonitrile 1600 ml/double-distilled water 400ml/trifluoroacetic acid 2 ml; mobile phase B: double-distilled water 2000 ml/trifluoroacetic acid 2 ml; gradient: A/B= 20:80%–80:20%; flow rate: 1.5 ml/min; T=45° C.). The results are shown in Table 3.

TABLE 3

| Inactivation | Content of [Leu$^1$, Thr$^2$]-63-desulfohirudin [%] | |
|---|---|---|
| temperature [°C.] | Start of test | End of test (after 8 days) |
| Original solution | 100 | 50 |
| 108 | 68 | 68 |
| 100 | 93 | 93 |
| 90 | 92 | 92 |
| 85 | 99 | 97 |
| 80 | 92 | 89 |
| 70 | 81 | 19 |

It will be apparent to those skilled in the art that various modifications and variations can be made to the processes and apparatus of this invention. Thus, it is intended that the present invention cover the modifications and variations of this invention provided they come within the scope of the appended claims and their equivalents.

This application claims the benefits of priority under 35 USC § 119 to German application 19529997.3, filed Aug. 16, 1995, the entire contents of which, including the specification, claims and abstract, are incorporated herein by reference. The contents of all of the patents, patent applications, and publications mentioned herein above also are incorporated by reference herein in their entirety.

What is claimed is:

1. A process for inactivating the carboxypeptidase Y (CPY) in a hirudin-containing culture broth, which comprises heating a culture broth comprising CPY and hirudin to a temperature of from about 80° C. to about 100° C. within about 60 seconds or less.

2. The process of claim 1, wherein said culture broth is heated past a temperature at which activation of the CPY occurs to a temperature of from about 80° C. to about 100° C., where inactivation of the CPY occurs, within about 60 seconds or less.

3. The process of claim 2, wherein said culture broth is heated past a temperature of about 70° C. to a temperature of from about 80° C. to about 100° C. within about 60 seconds or less.

4. The process of claim 1, wherein said culture broth is heated to a temperature of from about 80° C. to about 100° C. in from about 40 to about 60 seconds.

5. The process of claim 1, wherein said culture broth is heated to a temperature of from about 80° C. to about 100° C. in from 40 to 60 seconds.

6. The process of claim 1, wherein said culture broth is heated to a temperature of from about 85° C. to about 95° C.

7. The process of claim 1, wherein said culture broth is heated to a temperature of from 85° C. to 95° C.

8. The process of claim 1, wherein said culture broth is heated to a temperature of about 85° C.

9. The process of claim 1, further comprising the step of, after said heating step, cooling said broth to room temperature.

10. The process of claim 1, wherein said culture broth is a culture broth of transformed Saccharomyces cerevisiae.

11. The process of claim 1, wherein the pH of said culture broth is from about 6.2 to about 6.5.

12. The process of claim 1, wherein said culture broth is heated by microwave energy.

13. The process of claim 1, wherein said process comprises the steps of flowing said culture broth through a tubular apparatus comprising a heating section.

14. The process of claim 13, wherein the residence time of said culture broth in said heating section is from about 40 to about 60 seconds.

15. The process of claim 13, wherein the residence time of said culture broth in said heating section is from 40 to 60 seconds.

16. The process of claim 13, wherein said heating section comprises a flow-through heat exchanger whose inner surface is continuously mechanically cleaned.

17. The process of claim 13, wherein said tubular apparatus further comprises a holding section.

18. The process of claim 13, wherein said tubular apparatus further comprises a cooling section.

19. The process of claim 1, wherein said process comprises flowing said culture broth through a tubular apparatus comprising a heating section, a holding section and a cooling section.

20. A process for inactivating the carboxypeptidase Y (CPY) in a hirudin-containing culture broth, which comprises:

providing demineralized water as inflow into a flow-through tubular apparatus comprising a heating section;

heating the inflow in the heating section to a temperature of from about 80° C. to about 100°;

changing the inflow from water to a culture broth comprising CPY and hirudin while maintaining the temperature of the inflow in the heating section at from about 80° C. to about 100° C., such that the culture broth is heated to a temperature of from about 80° C. to about 100° C. within about 60 seconds or less.

* * * * *